United States Patent [19]

Wiedemann

[11] 4,115,457
[45] Sep. 19, 1978

[54] POLYGLYCOL ETHER DERIVATIVES

[75] Inventor: Achim Wiedemann, Weil am Rhein, Germany

[73] Assignee: Sandoz Ltd., Basel, Switzerland

[21] Appl. No.: 785,532

[22] Filed: Apr. 7, 1977

Related U.S. Application Data

[63] Continuation of Ser. No. 703,257, Jul. 7, 1976, abandoned, which is a continuation of Ser. No. 594,199, Jul. 9, 1975, abandoned, which is a continuation of Ser. No. 382,718, Jul. 26, 1973, abandoned, which is a continuation of Ser. No. 191,352, Oct. 21, 1971, abandoned.

[51] Int. Cl.$^2$ .................. C07C 43/02; C07C 41/02
[52] U.S. Cl. .................. 260/615 B; 252/351; 252/170; 8/137; 8/139
[58] Field of Search .................... 260/615 B

[56] References Cited

U.S. PATENT DOCUMENTS

| | | | |
|---|---|---|---|
| 2,870,220 | 1/1959 | Carter | 260/615 B |
| 3,324,035 | 6/1967 | Nankee et al. | 260/615 B |
| 3,340,309 | 9/1967 | Weipert | 260/615 B |
| 3,350,462 | 10/1967 | Leary et al. | 260/615 B |
| 3,372,201 | 3/1968 | Leary et al. | 260/615 B |
| 3,504,041 | 3/1970 | Weipert | 260/615 B |
| 3,567,784 | 3/1971 | Tsatsos et al. | 260/615 B |
| 3,752,857 | 8/1973 | Milligan | 260/615 B |

FOREIGN PATENT DOCUMENTS

| | | | |
|---|---|---|---|
| 1,207,777 | 10/1970 | United Kingdom | 260/615 B |
| 1,256,609 | 12/1971 | United Kingdom | 260/615 B |
| 1,267,217 | 3/1972 | United Kingdom | 260/615 B |

*Primary Examiner*—Howard T. Mars
*Attorney, Agent, or Firm*—Gerald D. Sharkin; Richard E. Vila; Thomas C. Doyle

[57] ABSTRACT

The invention provides novel polyglycol ethers of formula I,

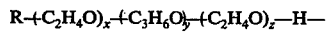

$$R\text{-}(C_2H_4O)_x\text{-}(C_3H_6O)_y\text{-}(C_2H_4O)_z\text{-}H\text{---} \qquad I$$

in which R is alkoxy of 8 to 24 carbon atoms,
 x has a value of 9 to 10
 y has a value of 12 to 17
and
 z has a value of 8 to 12.

The new compounds have a number of uses in the dyeing and printing industries, for example as scouring and washing agents.

8 Claims, No Drawings

POLYGLYCOL ETHER DERIVATIVES

This application is a continuation of copending application Ser. No. 703,257, filed July 7, 1976, now abandoned, which in turn was a continuation of application Ser. No. 594,199, filed July 9, 1975, now abandoned, which in turn was a continuation of application Ser. No. 382,718 filed July 26, 1973, now abandoned, which, in turn, was a continuation-in-part of application Ser. No. 191,352, filed Oct. 21, 1971, also abandoned.

The use of polyalkylene oxide adducts as scouring agents and dyeing assistants is known. It is desirable that such products should foam as little as possible, particularly when employed in jet dyeing machines, but should, at the same time, exert efficient wetting and detergent action. The present invention provides a novel class of polyalkylene oxide adducts which exhibit these desirable characteristics.

The present invention accordingly provides polyglycol ethers of formula I, $$R-(C_2H_4O)_x-(C_3H_6O)_y-(C_2H_4O)_z-H \qquad I$$

in which R is alkoxy of 8 to 24 carbon atoms,
 x has a value of 9 to 10,
 y has a value of 12 to 17,
and
 z has a value of 8 to 12.

In the preferred compounds, R suitably signifies a secondary alkoxy radical, in particular a secondary alkoxy radical of formula II, $$\underset{\underset{CH_3(CH_2)_m\overset{|}{C}H-O-}{}}{CH_3} \qquad II$$

in which m signifies an integer of 5 to 21.

Of particular interest, are secondary alkoxy radicals of 11 to 15 carbon atoms, for example those of formula II in which m is 8 to 12.

R may also suitably signify a primary alkoxy radical of 8 to 24, preferably 11 to 15, carbon atoms.

Specific alkoxy radicals which R may suitably signify include the following :- n-octyloxy, octyl-2-oxy, n-decyloxy, decyl-2-oxy, n-undecyloxy, n-dodecyloxy, dodecyl-2-oxy, n-tetradecyloxy, tetradecyl-2-oxy, heptadecyl-2-oxy, hexadecyl-2-oxy, behenyloxy, n-octadecyloxy, and, in particular, secondary alkoxy, eg. alk-2-oxy, radicals of 11 to 15 carbon atoms.

In the preferred compounds, y preferably has a value of 15 to 16.

The products of the invention may be produced in manner well-known for the production of polyglycol ethers, by reaction of a compound of formula III, $$R-H \qquad III$$

in which R is as defined above, with ethylene oxide, reaction of the product obtained with propylene oxide, and reaction of the product obtained with ethylene oxide in the molar ratio of 1:x:y:z, respectively.

It will be appreciated that a mixture of products may be produced so that the values of x, y and z may be average values. Furthermore, a mixture of alcohols of formula III may be employed, and, indeed, a mixture of secondary alcohols of 11 to 15 carbon atoms is employed to produce the preferred agents of the invention.

The reactions with ethylene and propylene oxide are suitably effected at a temperature of at least 100° C, preferably 140° to 200° C, more preferably 170° to 180° C. The reactions may, if desired or necessary, be effected in the presence of an alkaline or acid catalyst such as sodium or potassium hydroxide or carbonate antimony pentachloride, stannous tetrachloride or boron trifluoride etherate. The process may conveniently be carried out in the absence of air, for example under a nitrogen atmosphere, if desired at excess, but preferably normal, pressure. The reaction may suitably be terminated by introduction of nitrogen gas into the reaction mixture.

The products obtained are soluble in water and may suitably be stored and marketed in the form of concentrated aqueous solutions of, for example, 60 to 70% by weight, strength.

The products of the invention exhibit minimal foaming and are stable to acids, lyes and salts.

The products of the invention are useful for scouring textile materials prior to printing or dyeing. As is well-known, such a scouring step, is normally necessary to remove contaminants, eg. oils, fats and various other impurities, from textile materials prior to dyeing or printing, to ensure optimum take-up etc of the dye. For such use, the textile materials are suitably treated in an aqueous bath containing the products of the invention. Such aqueous bath preferably contains from 0.01 to 2%, more preferably 0.05 to 0.2% by weight, of the compound of formula I. The treatment is suitably effected at a temperature of from 20° to 100° C, preferably 40° to 80° C and for a period of from 10 to 60, preferably 20 to 30 minutes. The scouring is conveniently effected at a pH of from 5 to 10, preferably 8 to 9, in the presence of conventional additives such as tetrasodium pyrophosphate, ammonium sulphate, sodium carbonate, sodium sulphate and acetic acid, for adjusting the pH of the bath.

The products of the invention are also useful for washing off textile materials subsequently to dyeing or printing, particularly printing. Such an after treatment is often necessary to remove excess dye and other impurities, eg. dyebath additives, such as carriers, from the dyed or printed textile materials, prior to drying. For such use, aqueous solutions containing from 0.01 to 2%, preferably 0.05 to 0.2% by weight, of the product of formula I, are suitably employed. The washing off is suitably carried out at a temperature of from 15° to 90°, preferably 50° to 75° C, and for a period of from 10 to 60', preferably 20 to 30'. The pH of the aqueous solution is suitably from 5 to 10, preferably 8 to 9, conveniently adjusted by additions of such conventional agents as caustic soda and sodium hydrosulphite.

The products of the invention are also useful as dyeing assistants, eg wetting agents, in dyeing or printing, with, for example, disperse or reactive dyes, particularly in dyeing hydrophobic textile materials with disperse dyes. For such use, substantially smaller amounts of the compound of formula I may be employed then for scouring or washing off. For example, the dyebath or printing medium may suitably contain from 0.01 to 2%, preferably 0.05 to 2 % by weight of the compound of formula I.

A particularly useful embodiment of the invention combines the uses as scouring agents and dyeing assistants of the products of the invention. Thus, scouring and dyeing may suitably be carried out simultaneously in the same medium containing the product of formula I, under the conditions described above for scouring.

Alternatively, the textile materials may first be scoured as described above and then dyed in the same medium after addition of dye.

The textile materials for which the products of the invention are useful, may comprise synthetic, semisynthetic or natural high polymers. Examples include natural and regenerated cellulosic fibres, polyamide fibres, eg. wool, silk and synthetic polyamides, polyacrylonitrile, polyester and polyolefine fibres, of which polyester, wool and blended polyester and cotton or polyamide and polyacrylonitrile fibres are particularly noteworthy.

Textile materials treated with the compounds of the invention in wet processing, either before, during or after dyeing or printing, retain the fastness properties, particularly to rubbing, of the dyes employed. The products of the invention are advantageous for use in scouring in jet dyeing machines, for example the Gaston County Jet dyeing machines, because of their low tendency to foaming and noteworthy wetting and detergent action. Furthermore, because of the low foaming tendency, minimal dye is retained in disperse dyebaths containing the products of the invention, and good white reserve shown by unprinted areas in prints with disperse dyes may be achieved.

The following Examples, in which parts and percentages are by weight and temperatures in degrees Centrigrade, illustrate the invention.

EXAMPLE 1 (Production of Assistant I)

In the presence of 0.5% sodium hydroxide as catalyst, 928 parts (16 mols) of propylene oxide are added on 598 parts of a secondary $C_{11}$-$C_{15}$ alcohol mixture, obtainable from Union Carbide under the trade name Tergitol 15-S-9 previously reacted with 9 mols of ethylene oxide, after which 440 parts (10 mols) of ethylene oxide are added on, working at 170°–180° throughout, under normal pressure. The first addition reaction is carried out by slowly dropping the propylene oxide into the alcohol mixture in the absence of air and with thorough stirring. The second addition reaction is effected by introducing the liquid ethylene oxide into the propoxylated mixture and is completed by directing nitrogen into the mixture in place of ethylene oxide. The reaction mixture is then allowed to cool. Assistant I is obtained. It is free from foaming and has excellent detergent and wetting action for hydrophobic and natural textile fibres. The turbidity point of a 1 % solution of the product is 43°.

EXAMPLE 2 (Production of Assistant II)

In analogy with Example 1, 526 parts of octanol-(2), previously reacted with 9 mols of ethylene oxide, are reacted with 928 (16 mols) parts of propylene oxide and 440 parts (10 mols) of ethylene oxide. The product is Assistant II Octanol-(2) can be replaced by primary octyl alcohol. Assistant IIa is obtained EXAMPLE 3 (Production of Assistant III)

638 Parts of hexadecanol-(2) reacted with 9 mols of ethylene oxide are reacted with 928 parts (16 mols) of propylene oxide and 440 parts (10 mols) of ethylene oxide as described in Example 1. Assistant III is obtained.

EXAMPLE 4 (Production of Assistant IV)

582 Parts of dodecanol-(2) reacted with 9 mols of ethylene oxide are reacted with 920 parts (16 mols) of propylene oxide and 440 parts (10 mols) of ethylene oxide as described in Example 1. Assistant IV is obtained. The dodecanol-(2) can be replaced by dodecanol-(1), whereupon assistant IVa is obtained.

EXAMPLE 5 (Production of Assistant V)

554 Parts of decanol-(2) reacted with 9 mols of ethylene glycol are reacted with 928 parts (16 mols) of propylene oxide and 440 parts (10 mols) of ethylene oxide by the procedure of Example 1 to give Assistant V. The reaction can be carried out in an analogous manner using 722 parts of behenyl alcohol, or octadecanol-(1) in place of decanol-(2). The products are assistants Va and Vc respectively EXAMPLE 6 (Production of Assistant VI)

610 Parts of tetradecanol-(2) reacted with 9 mols of ethylene oxide are reacted with 928 parts (16 mols) of propylene oxide and 440 parts (10 mols) of ethylene oxide as described in Example 1. The product is Assistant VI. The tetradecanol-(2) can be replaced by tetradecanol-(1) which results in Assistant VIa.

EXAMPLES OF APPLICATION

The dyes used to perform the following Examples have the formulae given below.

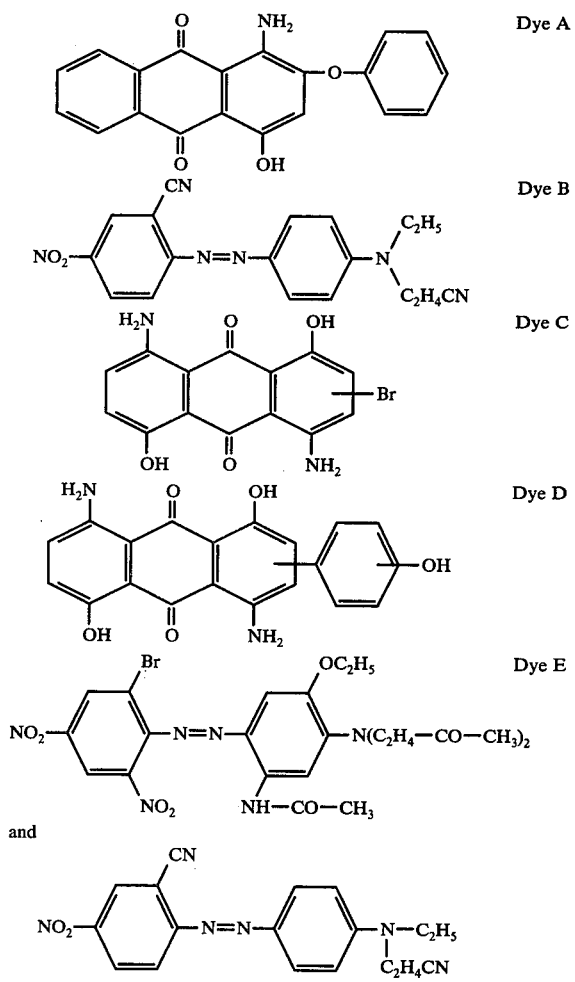

and

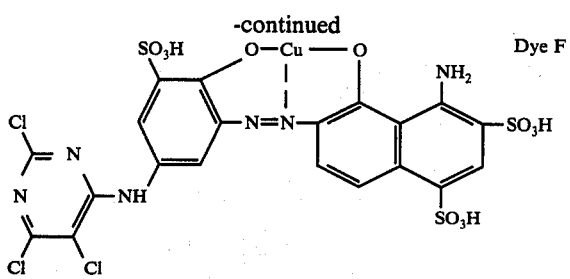

Dye F

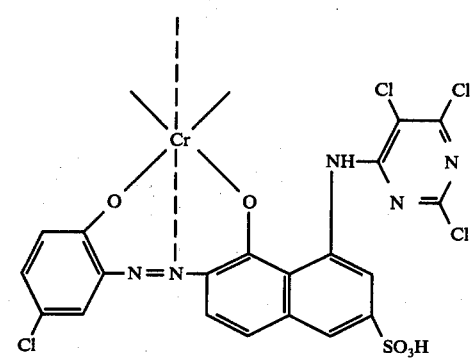

Dye G

Dye H

This is produced in accordance with German Pat. No. 1 039 992, column 5, lines 47-53, or by reaction of 1 mol of copper phthalocyanine tetrasulphonic acid chloride with 1-2 mols of the compound of formula

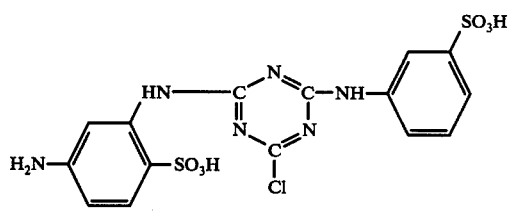

EXAMPLE 7

Washing off prints produced with disperse dyes:

A 67/33% polyester/cotton blend fabric is printed with 1000 parts of a paste containing 120 parts of dye B. The printed fabric is rinsed in the Launder-Ometer for 15 minutes with cold water, liquor ratio 100:1, and then washed off for 15 minutes at 60° with 2 g/l of an aqueous solution Assistant I. The unprinted areas of the fabric are reserved white. If washed off without Assistant I, the unprinted parts of the fabric are stained by the dye.

EXAMPLE 8

Example 7 is repeated with the same success using in place of dye B the same amount of dye C.

EXAMPLE 9

The polyester/cotton blend fabric of Example 7 is replaced by acetate twill, triacetate satin, or polyester fabrics, and the procedure of that Example repeated with equal success.

EXAMPLE 10

A 50/50% polyamide/cellulose triacetate blend fabric is printed with 1000 parts of a paste containing 120 parts of dye C. The printed fabric is washed off at liquor ratio of 20:1 in a bath set with a low-foaming aqueous detergent solution containing 0.2% of Assistant I, first for 30 seconds at room temperature, then for 60 seconds at room temperature and 60 seconds at 40°. The unprinted areas of the fabric are left with a white reserve

EXAMPLE 11

Combined scouring and dyeing procedure:

A textured polyester fibre, not previously scoured or set, is rinsed with cold water for a short time in the Gaston County jet dyeing machine. Then an 0.5 g/l aqueous solution of Assistant I is added and the rinsing water is heated to 70° at pH-9-10 for 30 minutes. The pH is adjusted to 5, the bath is set with 0.5% of dye A and its temperature raised to 125°. The fabric is dyed at this temperature for 45 minutes, rinsed and thermofixed at 150°. A level dyeing is obtained. No interference from foam occurs in scouring or dyeing.

Level dyeings are obtained when in place of Assistant I similar amounts of Assistant II, IIa, III, IV, IVa, V, Va, Vc, VI or VIa are present in the bath and one of the dyes B to G is employed in place of dye A.

EXAMPLE 12

Detergent power:

A 10 gram supply of a grey polyester fabric containing 5.8% oil is scoured in the Linitest apparatus for 30 minutes at 70° and liquor ratio 30:1 with 1 g/l of Assistant I and 2 g/l tetrasodium pyrophosphate (pH $\simeq$ 10). After subsequent rinsing its residual oil content is 0.3%.

Comparable scouring action is obtained when the bath is set with 2 g/l ammonium sulphate and acetic acid (pH $\simeq$ 5.5) in place of 2 g/l tetrasodium pyrophosphate.

EXAMPLE 13

An artificially soiled cotton fabric is scoured for 30 minutes at 95° in a bath containing 0.05% to 0.4% of the polyadduct described in Example 1 and 0.2% sodium carbonate. The fabric is photoelectrically measured before and after scouring and the difference in whiteness noted as a measure of the power of detergency. The product develops practically no foam, but it has excellent wetting and scouring action.

EXAMPLE 14

A wool fabric is dyed at liquor ratio of 40:1 in a bath containing 3% of dye H, 1.5% acetic acid, 10% sodium sulphate and 1% of Assistant I relative to the fabric weight.

The wool is first treated for 10 minutes at 50° in the bath without dye, after which the well dissolved dye is added. The bath is then brought to the boil in 45 minutes and the fabric dyed for 45 minutes at the boil. A level dyeing is obtained. Dyeings on wool showing comparable levelness are obtained with the aid of Assistants II or VI. If no assistant of the disclosed type is present in the bath, the dyeing is unlevel.

EXAMPLE 15

High-temperature dyeing of polyester fabric:

100 Parts of an unset polyester fabric are dyed for 30 minutes at 130° in an aqueous bath of 6000 parts containing 1.8 parts of the dye used in Example 3, 12 parts of ammonium sulphate and 2 parts of the compound described in Example 1. The polyglycolether is stable under high-temperature conditions in the presence of disperse dyes. After dyeing, the fabric is rinsed and washed off as in Example 16, hereafter. A level dyeing with very good rubbing fastness is obtained.

EXAMPLE 16

A fabric of textured polyester yarn contaminated with 6% of preparative oils is scoured for 30 minutes at 70° in the Gaston County jet dyeing machine in an aqueous bath containing 0.1% of the polyadduct of average molecular weight 1800°–2000 described in Example 1. The scouring bath is allowed to cool to 60° and the fabric rinsed. It is then dyed for 1½ hours at 120° in a bath set with about 1.5% of dye C, 3% aminosodium phosphate and 5% of a carrier containing 80% orthophenylphenol and 20% emulsifier. The dye-bath is cooled to 65° and the fabric rinsed and washed off for 20 minutes at 80° with 0.6% of the compound described in Example 1.2 % of caustic soda flakes and 3% sodium hydrosulphite. After the scouring bath has cooled to 65° the fabric is rinsed for 10 minutes with water. No interfering foam appears during scouring. The detergent action prevents spot formation on the dyed fabric.

What is claimed is:

1. A polyglycol ether of formula

in which
R is secondary alkoxy of 8 to 24 carbon atoms,
$x$ has a value of 9 to 10,
$y$ has a value of 12 to 17,
and
$z$ has a value of 8 to 12.

2. A polyglycol ether of claim 1, in which R is secondary alkoxy of 11 to 15 carbon atoms.

3. A polyglycol ether of claim 1, in which R is secondary alkoxy of formula

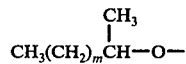

in which $m$ is an integer of 5 to 21.

4. A polyglycol ether of claim 3, in which m is 8 to 12.

5. A polyglycol ether of claim 1, in which $y$ is 15 or 16.

6. A polyglycol ether of claim 2, in which $y$ is 15 or 16.

7. A polyglycol ether of claim 3, in which $y$ is 15 or 16.

8. A polyglycol ether of claim 4, in which $y$ is 15 or 16.

* * * * *

UNITED STATES PATENT AND TRADEMARK OFFICE
CERTIFICATE OF CORRECTION

PATENT NO. : 4,115,457
DATED : September 19, 1978
INVENTOR(S) : Achim Wiedemann

It is certified that error appears in the above-identified patent and that said Letters Patent are hereby corrected as shown below:

Add the following claim:

-- 9. A polyglycol ether of claim 2 wherein x is 9, y is 16 and z is 10. --

Signed and Sealed this

Eighteenth Day of December 1979

[SEAL]

Attest:

SIDNEY A. DIAMOND

Attesting Officer

Commissioner of Patents and Trademarks